United States Patent
Sawyer et al.

(10) Patent No.: US 7,606,405 B2
(45) Date of Patent: *Oct. 20, 2009

(54) DYNAMIC TUMOR DIAGNOSTIC AND TREATMENT SYSTEM

(75) Inventors: Timothy E. Sawyer, Boise, ID (US); Thomas Edwin Payne, Bothell, WA (US)

(73) Assignee: ImQuant LLC, Boise, ID (US)

( * ) Notice: Subject to any disclaimer, the term of this patent is extended or adjusted under 35 U.S.C. 154(b) by 363 days.

This patent is subject to a terminal disclaimer.

(21) Appl. No.: 11/417,080

(22) Filed: May 3, 2006

(65) Prior Publication Data
US 2007/0014454 A1    Jan. 18, 2007

Related U.S. Application Data

(63) Continuation-in-part of application No. 10/910,711, filed on Aug. 3, 2004, now Pat. No. 7,343,030.

(60) Provisional application No. 60/677,750, filed on May 4, 2005, provisional application No. 60/534,633, filed on Jan. 7, 2004, provisional application No. 60/508,117, filed on Oct. 2, 2003, provisional application No. 60/492,796, filed on Aug. 5, 2003.

(51) Int. Cl.
*G06K 9/00* (2006.01)

(52) U.S. Cl. .................. 382/128; 382/131; 382/199; 378/65; 600/410

(58) Field of Classification Search .......... 382/118, 382/128, 131, 294, 132, 199; 378/98.9, 65, 378/205, 4, 207; 600/407, 427, 415, 425, 600/411, 426, 439, 431, 410, 436, 414, 1, 600/429, 443, 437, 401; 250/363.04, 363.03, 250/363.02, 252.1; 424/1.11, 1.65; 423/2, 423/510; 128/906; 540/145
See application file for complete search history.

(56) References Cited

U.S. PATENT DOCUMENTS

| | | | | |
|---|---|---|---|---|
| 5,317,616 | A * | 5/1994 | Swerdloff et al. | 378/65 |
| 5,376,795 | A * | 12/1994 | Hasegawa et al. | 250/363.04 |
| 5,509,412 | A * | 4/1996 | Bahn | 600/419 |
| 5,724,400 | A * | 3/1998 | Swerdloff et al. | 378/65 |
| 6,463,438 | B1 * | 10/2002 | Veltri et al. | 706/15 |
| 6,526,117 | B1 | 2/2003 | Okerlund et al. | |
| 6,611,630 | B1 | 8/2003 | Miller et al. | |
| 6,631,284 | B2 * | 10/2003 | Nutt et al. | 600/427 |
| 6,751,290 | B2 * | 6/2004 | Salb | 378/98.9 |
| 7,343,030 | B2 * | 3/2008 | Sawyer | 382/128 |
| 2001/0022853 | A1* | 9/2001 | Takaoka | 382/167 |
| 2002/0002472 | A1 | 1/2002 | Abraham-Fuchs | |
| 2004/0120557 | A1 | 6/2004 | Sabol et al. | |
| 2004/0210548 | A1 | 10/2004 | Ketcherside, Jr. et al. | |
| 2005/0041843 | A1 | 2/2005 | Sawyer | |
| 2006/0010090 | A1 | 1/2006 | Brockway et al. | |

* cited by examiner

*Primary Examiner*—Sheela C Chawan
(74) *Attorney, Agent, or Firm*—Quarles & Brady LLP

(57) ABSTRACT

A workstation imports medical images that depict a tumor and provides tools that enable a physician to see the results of prior therapies, plan future therapies, predict the outcome of future therapies and control future therapies. The workstation processes the imported images to produce isonumeric images of the tumor that can be analyzed by an expert system that provides diagnostic and outcome information as well as suggestions for further testing and therapy.

12 Claims, 8 Drawing Sheets

DYNAMIC TUMOR DIAGNOSTIC AND TREATMENT SYSTEM

CROSS-REFERENCE TO RELATED APPLICATIONS

This application is a continuation-in-part of U.S. patent application Ser. No. 10/910,711, filed on Aug. 3, 2004 now U.S. Pat. No. 7,343,030, which claims benefit of U.S. provisional patent applications Ser. Nos. 60/492,796 filed on Aug. 5, 2003, 60/508,117 filed on Oct. 2, 2003 and 60/534,633 filed on Jan. 7, 2004. This application also claims benefit of U.S. provisional patent application Ser. No. 60/677,750 filed on May 4, 2005 and entitled "Expert System for Image-Based Therapy and Diagnosis of Tumors."

BACKGROUND OF THE INVENTION

The field of the invention is medical imaging, and particularly, the use of medical imaging in the diagnosis and treatment of cancer.

Advanced imaging techniques for brain and other neoplasms acquire a variety of physiological data in addition to anatomic data. These include PET scanning, conventional MRI, MRI-spectroscopy, diffusion imaging, SPECT, perfusion imaging, functional MRI, tumor hypoxia mapping, angiogenesis mapping, blood flow mapping, cell death mapping and other methods. In addition, it is anticipated that new and better agents for use in SPECT, PET, and other imaging will be created and/or identified. These techniques will lead to an improvement in the ability to differentiate tumor from normal tissue.

Traditional display of physiologic images is in several ways insufficient. Physiologic images generated from sources such as PET and SPECT are indistinct (tumors have "blurry" borders), and are anatomically ambiguous. Fusion software has facilitated the viewing of neoplasms represented by PET and SPECT within the context of anatomic detail represented by CT. Integrated PET-CT and SPECT-CT devices have improved registration and fusion of anatomic and physiologic images. Traditionally, fused images are viewed by fading between CT and physiologic images, ranging from 0% CT/100% physiologic images, to 100% CT/0% physiologic images.

In present day treatment planning the creation of a three-dimensional treatment volume often involves the manual, slice-by-slice digital outlining of tumor on sequential tomographic images at a computer workstation. Computers are then used to convert cut-by-cut digital outlines into three-dimensional volumes, which become targets for surgical and/or radiation therapy planning. This process is labor-intensive. More importantly, however this process relies on the judgment of the person, usually a physician, digitizing the slice-by-slice images.

There are several limitations associated with the reliance on human judgment in this capacity. First, different physicians have different levels of experience in interpreting scans. Planning based on volumes generated by inexperienced physicians will be less accurate. Secondly, even for experienced physicians, interpretation of imaging findings is in many cases difficult, and in many instances based on "best guess" decision making. Even for experienced physicians, there will always be inter-observer variability. Thus, in research/protocol situations, outcomes data will not be directly transferable from institution to institution.

For imaging modalities such as spectroscopy or PET, particularly for tumors that invade adjacent structures or soft tissues, the line between tumor and adjacent non-tumorous structures is subjective and indistinct. This creates variability from cut to cut, patient to patient, and physician to physician. More importantly, however, it creates uncertainty with regard to the optimal volume needed to maximize local control while minimizing dose (and damage) to adjacent structures.

Traditional systems that display images or incorporate images into treatment processes consider images as physiologically homogenous. This is despite the fact that tumors are known to be physiologically heterogeneous. The limitations described above, related to display of a tumor's outer boundary, also apply to display of a tumor's internal heterogeneity.

Expert systems have been proposed for many medical applications. An expert system generates an inference based on a stored body of knowledge related to the disease and based on inputs in the form of test results and other information about the patient. Inference engines for expert systems come in many forms such as a Bayesian network, fuzzy logic, a decision tree, a neural network, or a self-organized map.

A Bayesian network includes a conditional probability-based network that relies on Bayes theorem to characterize likelihood of different outcomes based on known prior probabilities (i.e. observed prevalence of a disease) and newly acquired information (i.e. sensor signals). Bayesian networks use causal knowledge and explicitly model probabilistic dependence and independence relationships between different events.

Fuzzy logic provides a mechanism for manipulating uncertain information and variables that do not otherwise permit simple categorization as affirmative or negative. Fuzzy logic describes the application of if-then rules to uncertain information and provides probability of outcomes based on preceding events or conditions. Fuzzy logic relies on probabilistic if-then rules. According to principles of fuzzy logic, the probability that a premise will be true is predictable, and the conclusion that follows will also occur with some probability.

A decision tree provides a method for representing multiple temporal and logical inputs and the possible outcomes based on a combination of those inputs. A decision tree does not entail probabilities associated with branches.

A neural network is a black-box information-processing device having a number of non-linear processing modules connected together by elements that have information storage and programming functions. A self-organized map is a particular type sheet-like neural network array configured to execute an adaptive algorithm capable of learning. The neural network is based on the competitive and unsupervised learning process. Other types of expert systems are also contemplated.

While expert systems have been developed for many applications in the field of medicine, none have been developed for oncology. This is due in part to the fact that oncology is dependent on the analysis of medical images to evaluate the location, size, shape and growth of tumors. This critical information is needed for a proper diagnosis, outcome prognosis and treatment planning, and it is difficult to identify measurable parameters in images that can be input to an expert system.

SUMMARY OF THE INVENTION

The present invention is a system for receiving information regarding a tumor in a patient, which includes an expert system for diagnosing disease, predicting outcome, suggesting further testing, or suggesting therapy based on the received information and a stored knowledge base. Using such information as test results and patient information along with the medical images of the tumor, the system produces diagnostic, outcome, testing and therapeutic information that draws on the latest knowledge about the disease and its treatment.

One aspect of the present invention is the manner in which information in the form of medical images of the tumor are reduced to measurable parameters that are suitable for use as input to an expert system. More specifically, imported images are processed to produce isometric images that clearly indicate boundaries and other selected tumor parameters that may be used for analysis by expert systems. The tumor contour depicted in an isonumeric image has broad applicability to physiologic imaging techniques, including MRI, MR Spectroscopy (MRS), MRS Imaging (MRSI), perfusion imaging, additional functional MR techniques, PET, SPECT, and many other imaging processes. The combination of the isonumeric contour images, and expert system methods designed to analyze relationships between and changes in sets of isonumeric contours is superior to traditional methods of displaying images, and interpreting images.

The foregoing and other objects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE PREFERRED EMBODIMENT

The present invention may be implemented in a number of different ways. In the preferred embodiment it is implemented in a stand-alone computer workstation; however, it can be appreciated that some or all of the functions may be carried out in other systems such as imaging systems, PAC systems or therapeutic systems.

Figure 1:
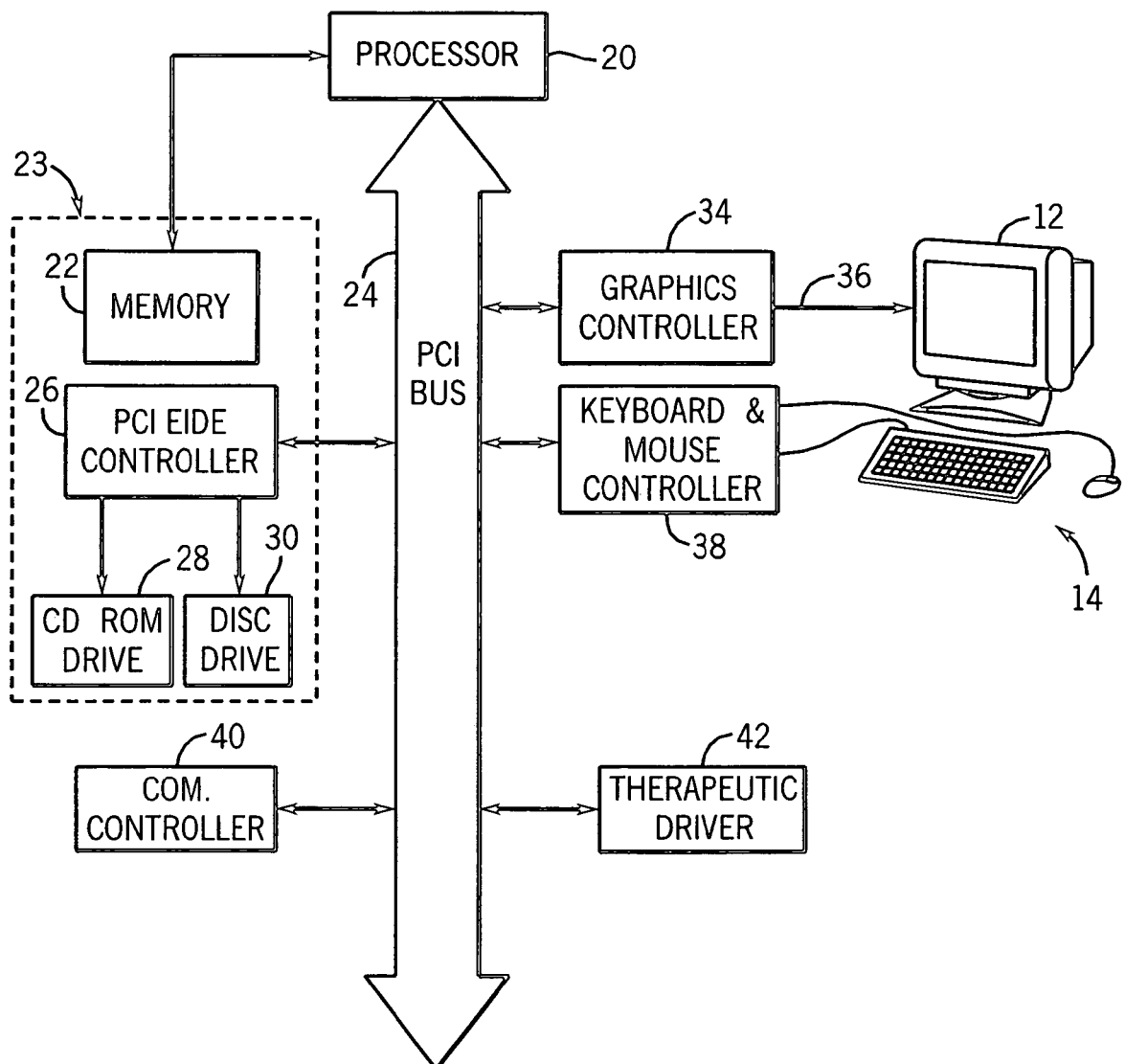
FIG. 1 is a block diagram of a workstation which is programmed to practice the preferred embodiment of the invention.

Referring particularly to FIG. 1, the computer workstation includes a processor 20 which executes program instructions stored in a memory 22 that forms part of a storage system 23. The processor 20 is a commercially available device designed to operate with one of the Microsoft Corporation Windows operating systems. It includes internal memory and I/O control to facilitate system integration and integral memory management circuitry for handling all external memory 22. The processor 20 also includes a PCI bus driver which provides a direct interface with a 32-bit PCI bus 24.

The PCI bus 24 is an industry standard bus that transfers 32-bits of data between the processor 20 and a number of peripheral controller cards. These include a PCI EIDE controller 26 which provides a high-speed transfer of data to and from a CD ROM drive 28 and a disc drive 30. A graphics controller 34 couples the PCI bus 24 to a CRT monitor 12 through a standard VGA connection 36, and a keyboard and mouse controller 38 receives data that is manually input through a keyboard and mouse 14.

The PCI bus 24 also connects to a communications controller 40. The controller 40 connects to an intranet that links the workstation to one or more imaging systems, a department PAC system, or an institution image management system. Images may be downloaded to the workstation from any source connected to the intranet, from the internet, or from a CD.

Optionally, the PCI bus 24 may also connect to a therapeutic system through a therapeutic driver card 42. Computer data may be output through the therapeutic driver to program a therapeutic system to treat a patient, or may be downloaded to CD.

Figure 2:
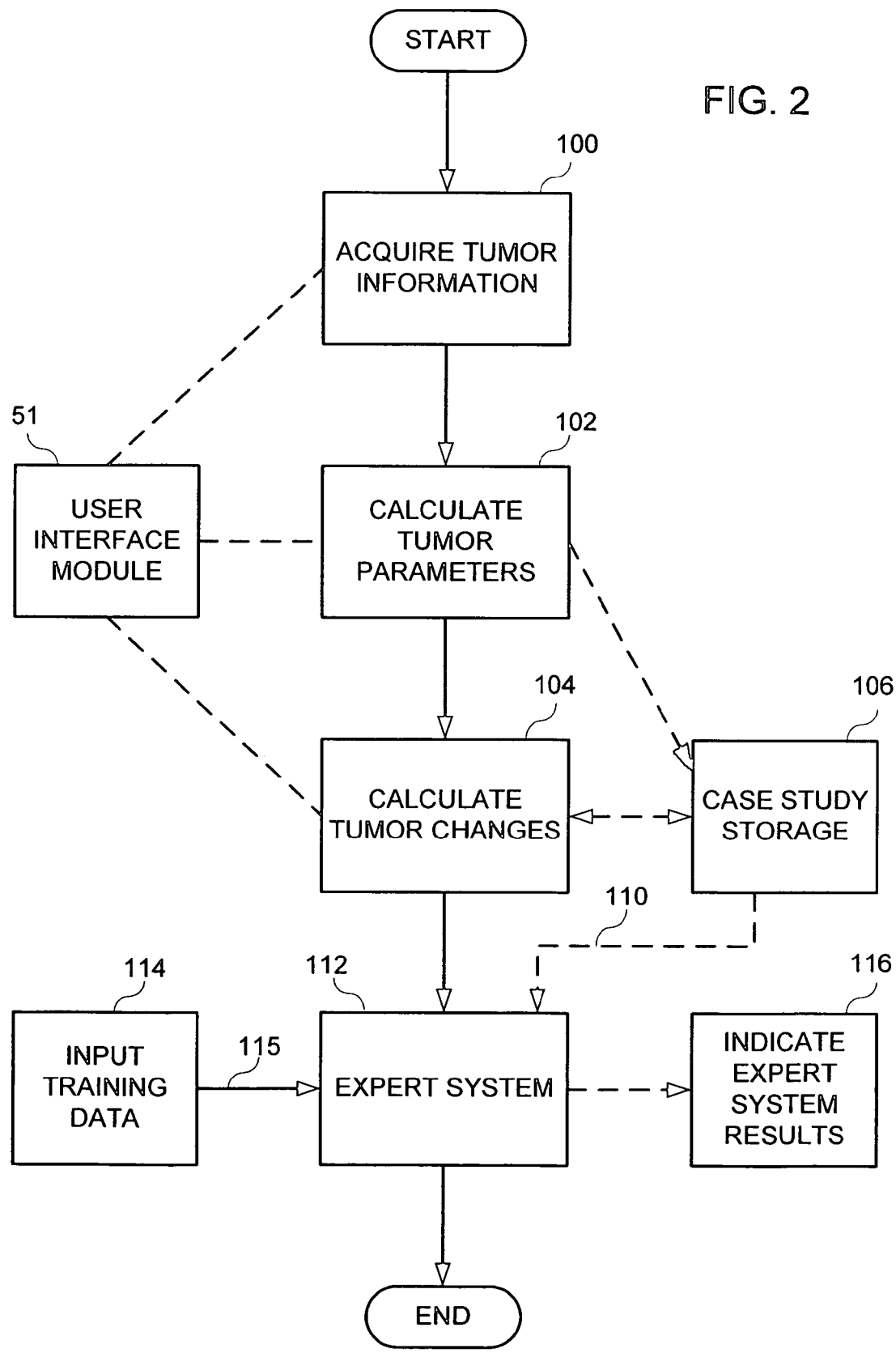
FIG. 2 is a flow chart of the software executed by the workstation of FIG. 1 to practice the present invention.

The dynamic tumor treatment system can be configured to perform a number of different functions in the treatment of cancer. As shown in FIG. 2, the configuration of the system and its operation are controlled through a user interface module 51 that prompts the user with information that is output to display 12 and receives user information input through the keyboard and mouse 14. In the preferred embodiment the system receives patient information including images from various sources as indicated at process block 100. These may include MR images, x-ray CT images, PET images, SPECT images or MR spectroscopy images. Images are registered for display with a system coordinate system. This enables images from different sources or different times during treatment to be imported and aligned with each other. Such registration may use fixed points in the acquired image or fiducials that are implanted in the patient for this purpose. Typically, an image modality is chosen that will contrast the particular tumor with surrounding tissue or that measures a parameter that characterizes the tumor. As an example, in FDG-PET imaging, radiolabelled glucose is preferentially taken up by tumor cells. As another example, ProstaScint binds to PSMA (prostate specific membrane antigen), which is over expressed in prostate cancer. Other non-image clinical data regarding the patient is also imported for use in later analysis. As an example, for the prostate cancer surgical planning application described later in this document, ProstaScint-based isonumeric contour data, the serum PSA value, the biopsy Gleason score value, and the clinical stage can be combined in a prognostic factor model used to predict the likelihood of extra-capsular extension or cavernous nerve involvement. As another example, when analyzing changes in isonumeric contours and contour relationships to predict the likelihood of lung cancer complete response to chemotherapy, factors such as tumor histology and tumor grade can be input.

Figure 5A:
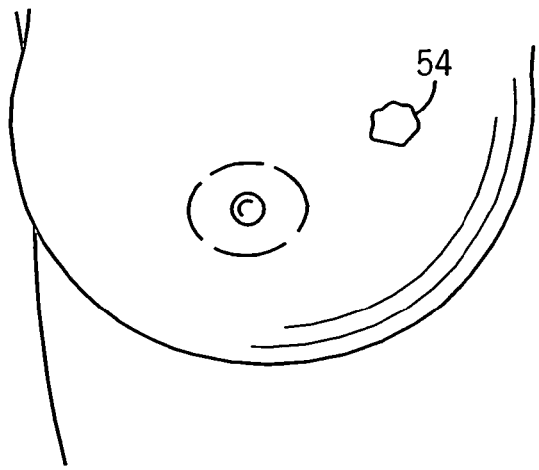
FIGS. 5A-5C are pictorial representations of an isonumeric image of a tumor boundary.
Figure 5B:
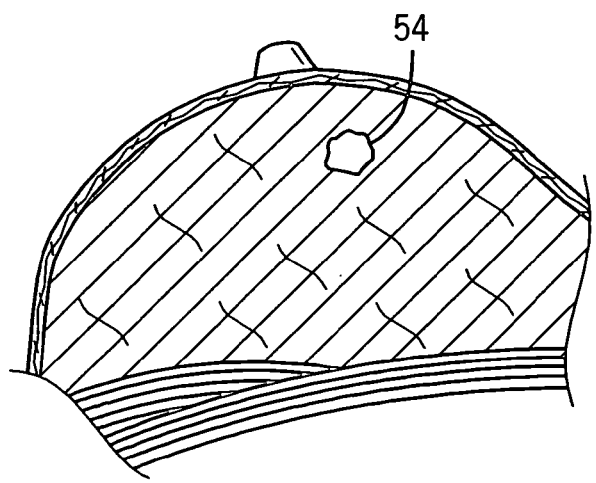
Figure 5C:
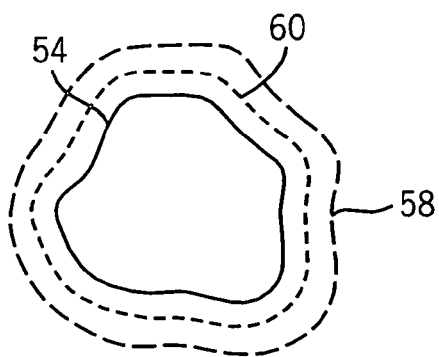
Figure 6:
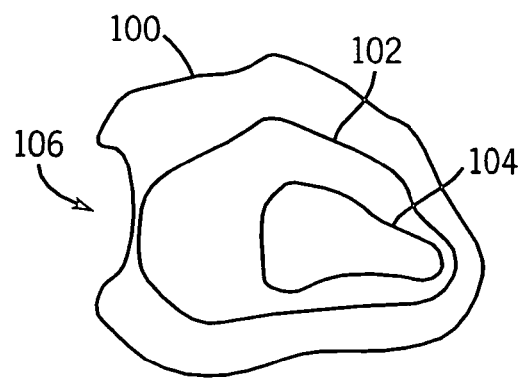
FIG. 6 is a pictorial view of three, registered isonumeric images of a tumor boundary at different treatment stages.

As indicated at process block 102 a second step is to calculate tumor parameters from the received information. An important aspect of this step is to produce an isonumeric image using the imported images. As will be discussed in more detail below, an isonumeric image is comprised of one or more contours which indicate a selected threshold level of a measured tumor parameter in the image. For example, the parameter may be FD-glucose uptake in a PET image, and the selected intensity level is a threshold of gamma radiation level which indicates the presence of a tumor in the human breast. The isonumeric contour can be viewed as a three-dimensional, closed contour surface which defines a boundary in three-dimensional space, or it can be viewed as a two-dimensional, open or closed contour line which defines a boundary in two-dimensional space. A set of three-dimensional isonumeric contours, of varying threshold values, can be sliced to form a series of two-dimensional contour lines. As shown in FIGS. 5A and 5B, an isonumeric contour line 54 may be displayed on the anatomical image to indicate where in the anatomy the tumor is located. As shown in FIG. 5C, the same isonumeric contour line 54 can be displayed separately from the anatomy in much larger scale in order to better see the details of its shape.

The acquired isonumeric image is analyzed at process block 102 to produce parameters that are valuable in recommending or planning further treatment. More specifically, characteristics related to the tumor as defined by the isonumeric contour image, including characteristics of individual contours and characteristics related to relationships between contours, are-calculated. These may include the following: calculate volume of each contour; calculate surface area of each contour; calculate shape characteristics; calculate median, mean, peak intensity values for voxels confined within a contour-defined volume; calculate contour distances from reference points or center; calculate distances of contours from each other; calculate volumes of contours containing contours of progressively increasing intensity ("elevations"); calculate volumes of contours containing contours of progressively decreasing intensity ("depressions"); calculate differences in threshold intensity levels, maximum or minimum intensity level within elevation or depression, versus contour representing base of depression or elevation; calculate locations of depressions and elevations; and calculate range or average thickness of contours. These are only a sampling of the calculations that may be made employing the isonumeric images. All the calculated parameter values are stored in the case study storage 106. In one embodiment of the present invention, the case study storage 106 is implemented as a commercially available spreadsheet, such as Microsoft Office 2003 Excel, or a commercially available database, such as Microsoft Office 2003 Access or Microsoft SQL Server, and is accessed via an industry standard interface, such as XML or CSV. One skilled in the art will recognize that there are other possible storage implementations, and that there are advantages to using standard access interfaces to retain maximum flexibility. Case study storage 106 can be a database local to and managed by a single clinic, or it may be a database managed by a centralized group and made available to clinics over the Internet. It can be accessed either locally, or remotely using a local area network, a wide area network, or a virtual private network using well-known techniques.

The treatment of cancer is an iterative process in which a therapy is repeatedly employed and the tumor is repeatedly tested, imaged and analyzed. These acquired tests and images and their corresponding isonumeric images are stored in case study storage 106. As shown in FIG. 5C, the isonumeric images from a series of such images may be registered with each other and displayed to reveal and analyze the changes that resulted from the therapy. In the example shown in FIG. 5C, the tumor has shrunk in size from an initial acquisition indicated by dashed line 58 and a first treatment indicated by dotted line 60. These and other changes are calculated at process block 104 and stored in the case study storage 106.

Figure 7:
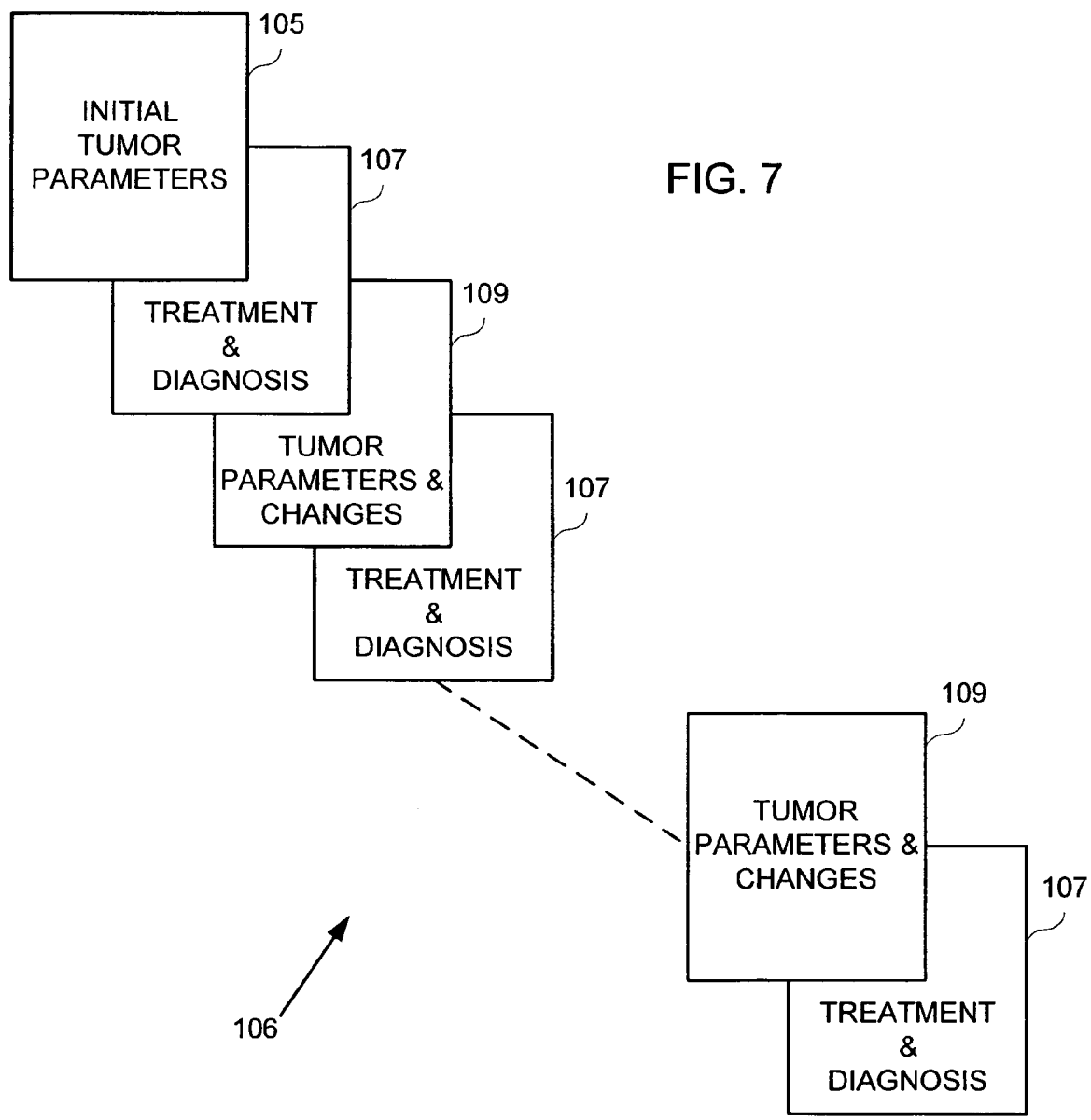
FIG. 7 is a pictorial representation of the case study storage that forms part of the software of FIG. 2.

As shown in FIG. 7, the case study storage 106 provides a history of the iterative treatment process that is characteristic of cancer treatment. It includes a record 105 of the initial tests and images and resulting tumor parameters that are stored at the beginning of the process. This is followed by a treatment and diagnosis record 107 that is stored following the analysis described below and prior to the next round of tests and images. Following the next round of tests and images, a tumor parameters and changes record 109 is stored and this is followed by another treatment and diagnosis record 107. Records 109 and 107 continue to be alternately stored as long as patient treatment continues. A preferred embodiment of the initial tumor parameters record 105 is shown in Table 1.

TABLE 1

TUMOR PARAMETERS

IMAGE PARAMETERS

Modality
        Image type
        Image interval (i.e. pre-treatment, prior to cycle n of chemotherapy, prior to
        fraction x of radiation therapy, etc.)
            Entire image
            Isonumeric image
            Volume (cc)
            Surface area (sq cm)
            Maximum Diameter (cm)
            Peak Intensity Value (SUV)
            Average Intensity Value (SUV)
            Median Intensity Value (SUV)
            Average distance of border from next contour (contour 2) (cm)
            Average distance of contour 2 from contour 3 (cm)
            Average distance of contour 3 from contour 4 (cm, 0 if not applicable)
            Average of average distance of first three contours to next inner
            contour (cm)
            Average of average distance of each contour to next inner contour (cm)
            Average volume of each contour (cc)
            Average surface area of each contour (sq cm)
            Number of non-contiguous elevated sub-volumes (number)
            Maximum height of an elevated sub-volume (SUV, 0 if not applicable)
            Average height of elevated sub-volume (SUV, 0 if not applicable)
            Maximum volume of an elevated sub-volume (cc, 0 if not applicable)

TABLE 1-continued

TUMOR PARAMETERS

Average volume of elevated sub-volumes (cc, 0 if not applicable)
Maximum distance of highest elevated sub-volume base to sub-volume center (cm, 0 if not applicable
Sub-volume 1 isonumeric image
    Volume (cc)
    Peak intensity value (SUV)
    Elevation of sub-volume 1 (SUV)
.
.
.
Sub-volume n isonumeric image
    Volume (cc)
    Peak intensity value (SUV)
    Elevation of sub-volume n (SUV)

NON-IMAGE PARAMETERS

Organ or tissue of origin
Histology
Stage
Tumor grade
Laboratory values
Patient age
Performance status values
Weight and other vital signs
Trend data for weight and other vital signs
Ethnicity
Sex
Family history
Pharmacogenomic data
Other generic information

ESTABLISHED TREATMENT REGIMENS

Established chemotherapy regimens
Established radiation therapy regimens

---

Figure 8:
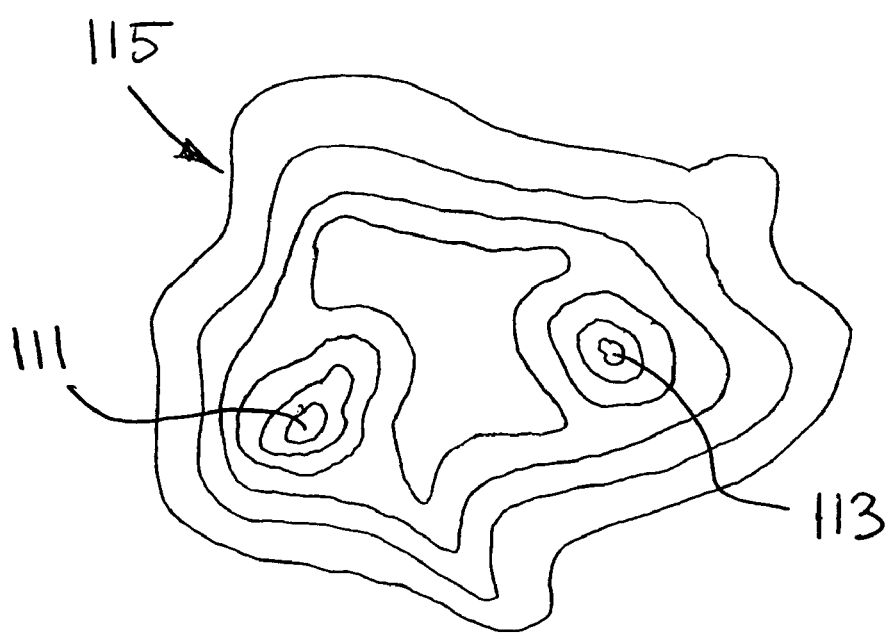
FIG. 8 is an isonumeric contour image of a tumor having two sub-volumes.

The "modality" field indicates the imaging modality used, such as MRI, MRS, SPECT, or PET. The "type" field indicates the particulars of the image scan that is performed to produce the "entire image" that is stored. As is evident, the generation of an isonumeric image enables a long list of tumor parameters to be calculated and stored. Parameters that can be calculated and stored are not limited to the above list. Of particular note is the ability to identify sub-volumes within the tumor boundary which enclose distinct peaks or valleys in the image as shown at 111 and 113 in the isonumeric image 115 in FIG. 8. Parameters are calculated and stored for each of these sub-volumes because it has been discovered that separate treatment may be required for a sub-volume within a tumor. For example, chemotherapy may be prescribed for the tumor, but additional radiation therapy may be indicated for a sub-volume therein.

Hence, an entire tumor or other region of interest, along with sub-regions of the tumor or region of interest, can be represented by a set of numbers. Change can be represented similarly. However, in any particular case study, only certain ones of the tumor parameters will have clinical significance. These significant parameters are determined by a pre-determined expression model, ROI (region of interest) expression model, or change expression model. These are pre-determined in accordance with research showing which parameter changes can be measured consistently and which are clinically meaningful. These expression models are input to the expert system 112 as will be described below.

By way of example, a patient has squamous cell carcinoma of the right tonsil, represented by FDG-PET-based standardized uptake values (SUVs). The primary tumor is bulky, and is radiographically contiguous with enlarged ipsilateral retropharyngeal and jugulodigastric lymph nodes. The significant tumor parameters for such a patient receiving cetuximab chemotherapy may be:

Volume (cc)
Peak Intensity Value (SUV)
Average Intensity Value (SUV)
Average of average distance of thirst three contours to next inner contour (cm)
Number of non-contiguous elevated sub-volumes (number)
Volume of largest elevated sub-volume (cc, 0 if not applicable)
Volume of 2nd largest elevated sub-volume (cc, 0 if not applicable
Volume of 3rd largest elevated sub-volume (cc, 0 if not applicable)
Average volume of elevated sub-volumes (cc, 0 if not applicable)
Height of largest elevated sub-volume (SUV, 0 if not applicable)
Height of 2nd largest elevated sub-volume (SUV, 0 if not applicable)
Height of 3rd largest elevated sub-volume (SUV, 0 if not applicable)

The numbers, sets of numbers, graphs, and equations representing pre-therapy isonumeric contours or contour sets stored in case study storage 106 can then be compared to numbers, sets of numbers, graphs, or equations from intra-therapy or post-therapy images. Changes can similarly be represented as numbers, sets of numbers, graphs, or equations. In response to therapy (such as chemotherapy or radiation therapy) a tumor's physiology may change significantly, without a significant change in the size, surface area, or shape of a contour representing only the tumor's outer boundary, especially early in therapy. Therefore, numeric and morphologic parameters of multiple isonumeric contours within an image, as well as the numeric and spatial relationships between such isonumeric contours within an image, can be analyzed. The results of such an analysis can be represented by a number, a set of numbers, graphs, or equations and used by the expert system as will be described below. Changes in isonumeric contour parameters (and other parameters) can be grouped conceptually into buckets, such as 0-20% change, 21-40% change, 41-60% change, and so on.

Figure 4:
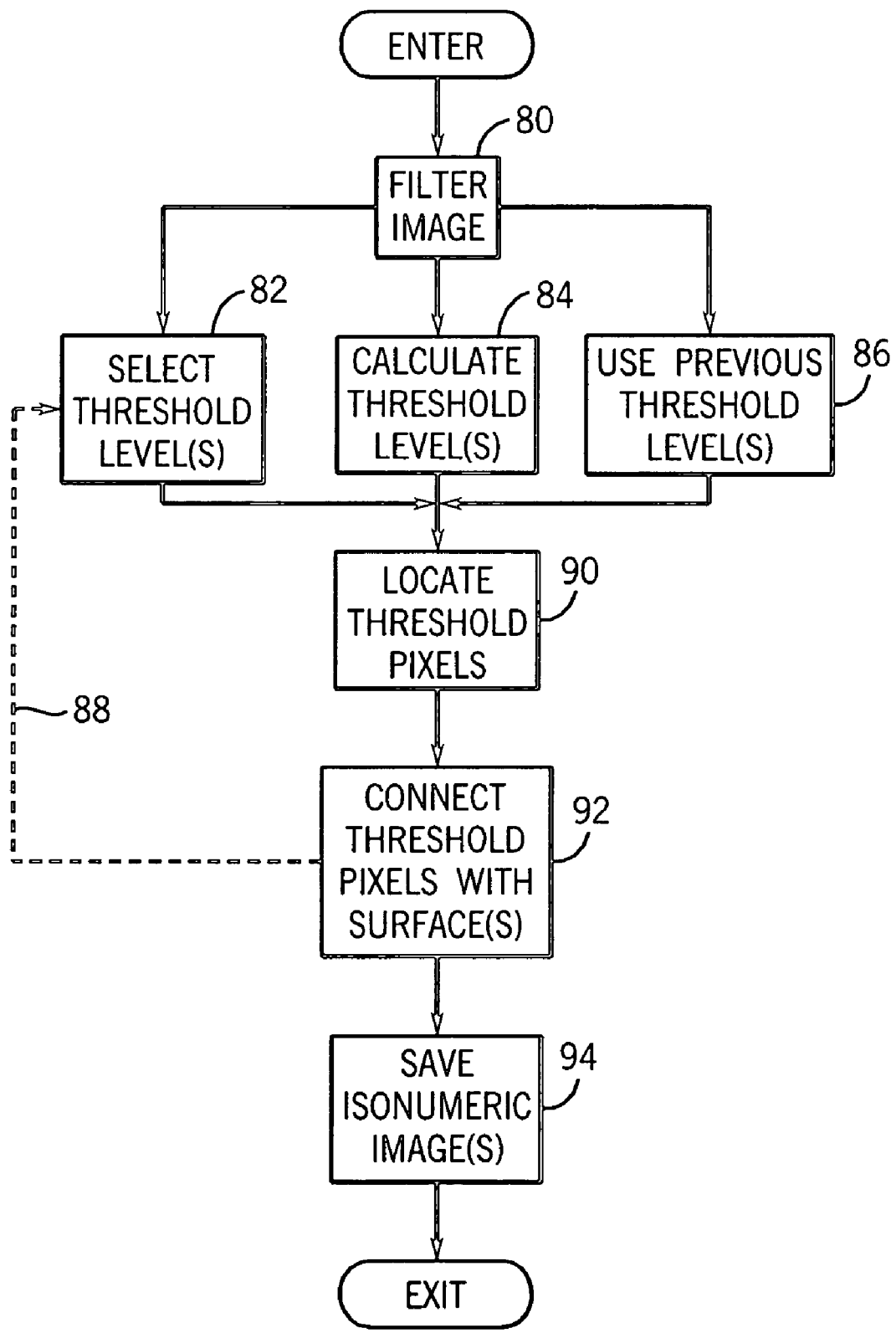
FIG. 4 is a flow chart of the method for producing an isonumeric image which forms part of the software of FIG. 2.

Referring particularly to FIG. 4, the production of an isonumeric image can be accomplished in a number of ways. As indicated at process block 80, most medical images require filtering to improve the results and reduce the processing time. For example, this step gives the user the option of selecting a region in the image for processing rather than processing the entire image. The user draws a line or creates a box around the region containing the tumor, making sure to allow ample space around its boundary.

As indicated by process blocks 82, 84 and 86, one or more threshold levels are then determined. As described above, the threshold level determines the voxels that have a tumor parameter value through which the isonumeric contour is drawn. As indicated at process block 82 this threshold level may be selected manually. For example, with a pancreatic tumor that is imaged with FDG-PET, the tumor boundary level may be set in an iterative process in which different threshold levels are selected and the resulting isonumeric contour is examined to see the relationships between the target (pancreatic tumor) and critical radiosensitive structures, such as the duodenum. This iterative process is indicated in FIG. 4 by dashed line 88.

As indicated by process block 84, the threshold level(s) can also be calculated, based on mathematical or clinical significance related to the diagnostic or therapeutic intervention chosen. Such values can be calculated by examining the acquired image itself, by examining other acquired images, or by using other clinical data such as pathology data or the like. For example, research may determine that a contour delineating the outer border of area within a non-small cell lung cancer that should be "boosted" with stereotactic irradiation, is of no clinical significance for a small-cell lung cancer, due to the much greater radiosensitivity and chemosensitivity of small cell lung cancer, relative to non-small cell lung cancer. Research may show that for non-small cell lung cancer, a "hot" area within a tumor is clinically relevant even if the difference in intensities between the hot area and the rest of the tumor is relatively small. On the other hand, it may be determined that for a hot area to be significant enough to require boost irradiation (and, therefore, automatic contour display) in small cell lung cancer, the difference in threshold values for the hot area versus the rest of the tumor must be much greater, even if the hot area for small cell lung cancer is defined by a contour of minimal spatial or volume difference from adjacent contours.

And finally, as indicated by process block 86, previously determined threshold values(s) may be used. This is normally the case when the current examination is the second or later iteration in the treatment process. In this case the change in the tumor due to the last round of therapy is of paramount importance and the same threshold level(s), normalized if necessary, should be used to measure that change.

After the threshold level(s) has been set, the image data are examined as indicated at process block 90 to locate those voxels at this level(s). This is done by comparing the value of each image voxel with a threshold level and building a separate bit map image in which voxel locations having the threshold level are set to "1" and all other voxels are reset to "0". Rather than a single threshold value, however, a small range of values around the threshold level can be accepted. The size of this range is set to a default value, but it can be adjusted by the operator and the step repeated to obtain the best possible contour. The resulting bit map image(s) will reveal the outline of the tumor at the threshold value. This is repeated for each threshold value such that a bit map image is produced for each. These bit map images are then combined into a single image in which each contour is displayed with a different color to keep them separate.

In many clinical applications the threshold value is compared directly with the image voxel values as described above. However, there are also clinical applications where the image voxel values are processed in some manner before the comparison is made. For example, in multi-slice and 3D magnetic resonance spectroscopic imaging, voxel intensity levels are proportional to molecular concentrations. Isonumeric contours can be created, for which the thresholds chosen represent particular concentrations of a particular molecule. Since studies have shown that ratios of molecular concentration are particularly important in distinguishing tumor from normal tissue, ratios between two molecules for each voxel can be calculated. Isonumeric contours can be created based on the ratios of intensity values (concentrations), rather than the intensity values themselves. Hence, image data can be "raw" (i.e. direct DICOM data); normalized (such as MRSI data that have been normalized to reflect metabolite concentrations, or PET data expressed as standardized uptake values); otherwise mathematically manipulated (such as MRSI data expressed as a sum or ratio of metabolite concentrations); or even "grouped" such as metabolite concentration ratios that have been placed into one of several categories (assigned numerical values 1-6, for example) based on the likelihood that cancer is present. Any data in which each voxel is represented by a set of three-dimensional coordinates and an intensity value is applicable. Such data can even be text-based, such as that entered from a standard spreadsheet (such as Microsoft Excel). Preferably, the data sets used are three-dimensional. However, technology described herein is also applicable to two-dimensional data sets. In any case, the comparison is made between the selected threshold and voxel values derived from the imported image. It should also be apparent that more than one tumor parameter may be used to produce the isonumeric image. For example, a threshold may be selected from an FDG-PET image indicating a region of high metabolic activity within a tumor, while a threshold may be selected from tumor hypoxia imaging indicating a region of hypoxia. Since the FDG and tumor hypoxia images are registered with each other, these contours can be overlaid upon each other, or upon an anatomic image. These isonumeric contours can also be combined into a single 3D contour for targeting purposes.

Due to a number of factors, including image noise, the bit map image at each threshold will usually not be a continuous 3D surface, but instead, it will show portions of such a surface with missing parts and it will have many disconnected, or stray voxels set to "1". As indicated at process block 92, the next step is to connect "set" voxels to form a continuous 3D surface and reset the stray voxels that are not a part of this surface. This is accomplished by first resetting stray voxels that are disconnected by examining the state of surrounding voxels. If all the voxels surrounding a set voxel are reset, it is considered a stray and it is reset. This filtering is repeated to identify stray groups of 2 through n voxels, where they are surrounded by 2 through n layers respectively of reset voxels. The value of n can be adjusted upward and the step repeated until the stray voxels are removed from the bit map images(s). Then, the remaining set voxels are used in an interpolation process to fill in any missing portions of the 3D contour surface. A cubic spline interpolator is used for this step. As indicated at process block 94, the resulting isonumeric image is then saved in case study storage 56.

It should be noted that more than one isonumeric contour may result from a single threshold applied to a heterogeneous tumor image. This can occur at many different thresholds when the tumor is more in the nature of two or more side-by-side tumors, but it is more common to see multiple isonumeric contours in a single tumor at a high threshold value. In such cases each isonumeric contour indicates those locations as sub-volumes in the tumor where the measured tumor parameter has reached peak values above the threshold.

Since the isonumeric image is derived from the original imported image, it is registered with that image. Therefore, the isonumeric image stored in the case study 106 may be easily merged with the original imported image also stored in the case study 106 or any other "anatomic" image or system that is registered therewith.

Referring again to FIG. 2, an expert system 112 is entered after the case study storage 106 is updated with the latest information. The expert system 112 is configured by the user interface module 51 to perform any of a number of functions that will be described in detail below. The expert system 112 uses its own knowledge base that is received as training data 114 and input at 115 along with information from the case study storage 106 that is input at 110 to produce expert system results as indicated at 116. As will be described in more detail below, the indicated results 116 may provide diagnostic information, provide an indication of probable outcome, an indication of further testing, and provide a plan for further treatment.

Figure 3:
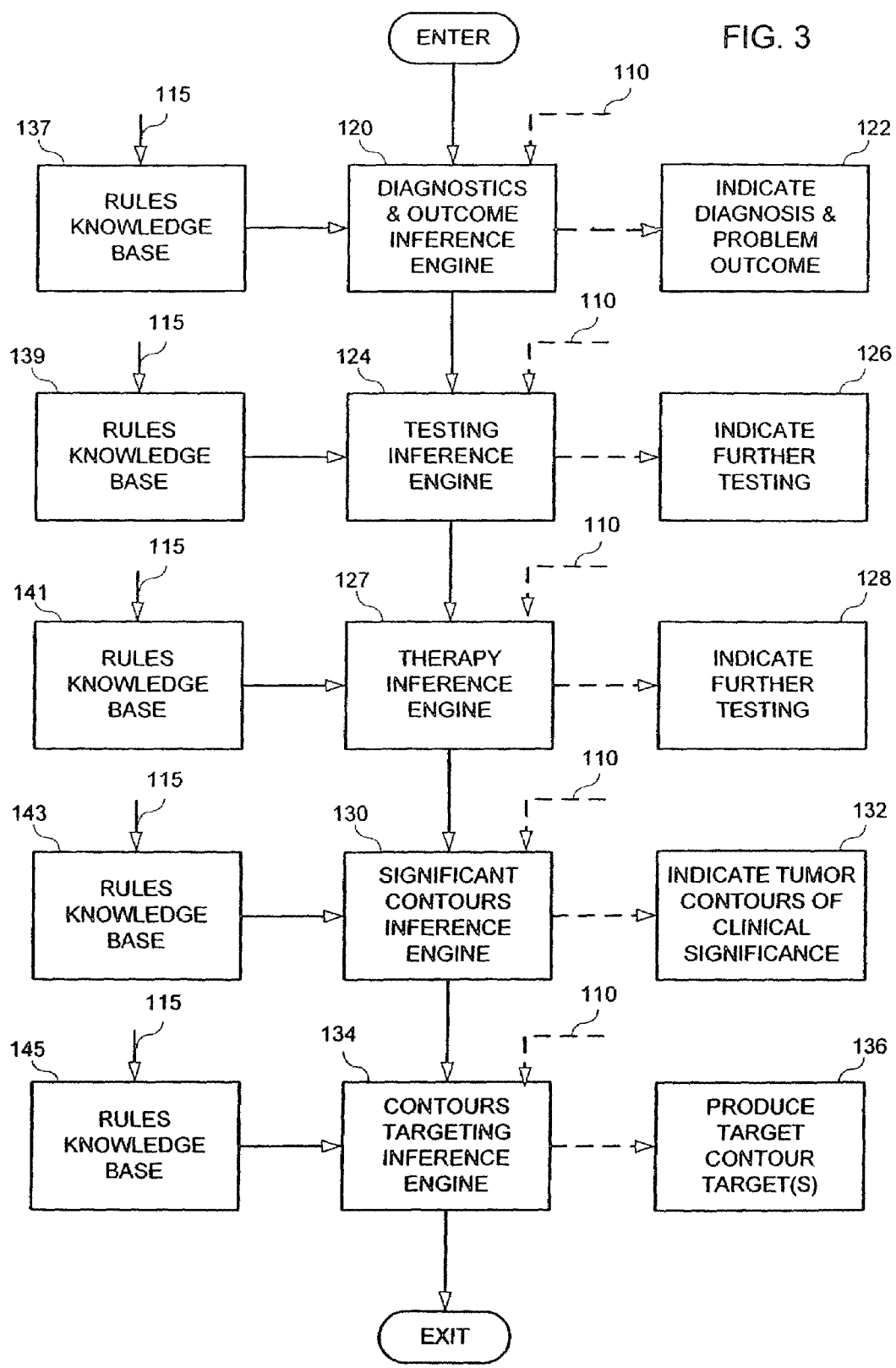
FIG. 3 is a flow chart of the expert system which forms part of this system of FIG. 2.

Referring particularly to FIG. 3, the expert system 112 includes up to five inference engines 120, 124, 127, 130 and 134 supported by up to five corresponding knowledge bases 137, 139, 141, 143 and 145. When configured through the user interface module 51 any one or more of these five separate inference engines may be used in any particularly clinical application. For example, a radiologist or urologist who discovers the tumor may employ only the diagnostics and outcome inference engine 120 and the testing inference engine 124, whereas the oncologist is more likely to employ the therapy inference engine 127, the significant contours inference engine 130 and the contours targeting inference engine 134.

All of the inference engines in the expert system 112 apply rules stored in its associated rules knowledge base to specific tumor parameters stored in the case study storage 106 and take action or provide an indication based on the outcome. The rules are in the form of an if-then statement in which selected tumor parameters are examined and "if" they meet certain conditions, "then" a specified action results.

The rules stored in the knowledge bases 137, 139, 141, 143 and 145 are derived from the latest research and knowledge regarding cancer. The rules knowledge bases may be resident in the work station memory 23, or they may include knowledge bases available through an organization's intranet or from anywhere in the world through the Internet. These rules are formulated by medical experts and are augmented over time as more discoveries are made. For example, the results of clinical trials may recommend the changing or adding of rules regarding the treatment of various types of cancer.

Training programs may also be used to create the rules and keep them up to date. For example, the training system will receive outcome information indicating that when the volume of a particular tumor type is reduced by X % when treated with a particular chemotherapy, there is a 70% chance that the tumor will be successfully treated. This information is used by the training programs to modify existing rules or it might be used to create one or more new rules. For example, the diagnostics and outcome inference engine 120 would employ such a rule to examine the case study storage 106 to learn if the tumor is of the particular type and to learn if the tumor volume has diminished X % after treatment with the particular chemotherapy. If so, a 70% probable successful outcome is indicated at process block 122. Of course, if the tumor type is not known, or the particular chemotherapy not tried, then this rule will not result in any action by the diagnostics and outcome inference engine 120. Inference engine 120 is used to make predictions regarding therapeutic outcome, and in the diagnostic realm, to provide diagnostic percent likelihood values. Outcomes can include end-therapy isonumeric contour profile, end-therapy complete radiographic tumor resolution, two-year disease free survival, or any other radiographic or clinical endpoint. In addition to displaying the results, diagnostic likelihood values are stored in case study storage 106 for use by inference engines. For illustration purposes, a series of clinical examples are given.

INFERENCE ENGINE 120 EXAMPLE 1

The patient with tonsil cancer detailed above in paragraph [0039] is referred to. If the patient has stage III disease, if the site of origin is the tonsil, if the patient has squamous cell histology, if the full planned established treatment regimen consists of 2 cycles of cetuximab chemotherapy followed by intensity modulated radiation therapy (consisting of 70 Gy in 35 fractions) with concurrent weekly cisplatin and cetuximab, if the imaging modality is FDG PET, if the patient undergoes intra-therapy imaging just prior to cycle 2 of cetiximab, and if the volume of the largest elevated sub-volume has only been reduced by 21-40%, then there is only a 50+/−5% likelihood of complete resolution of abnormal FDG uptake on the 4-month post-therapy PET scan. For the purpose of explanation, only one change parameter (volume of largest elevated sub-volume) is utilized in the above example. In actuality, a plurality of selected parameters can be utilized, such as all of the parameters in a particular change expression profile as explained above in paragraph [0038].

INFERENCE ENGINE 120 EXAMPLE 2

If all of the criteria in EXAMPLE 1 are met, except that the patient undergoes a second intratherapy imaging procedure after fraction 15 of radiation therapy and there is only a 41-60% change in the height of the largest elevated sub-volume, then there is only a 40% chance of 2-year disease-free survival.

INFERENCE ENGINE 120 EXAMPLE 3

If a patient has prostate cancer, if the histology is adenocarcinoma, if the stage is T2 N0, if the Gleason score is 6-7, if the pre-treatment serum PSA is 10.01-20, if the imaging modality is MRSI for which each voxel is represented by text-based data for which intensity values 1-6 have been assigned to each voxel in accordance with the likelihood that cancer is present, if the patient is receiving an established intensity modulated radiation therapy regimen consisting of an established regimen of 81 Gy in 45 fractions, if intra-therapy MRSI imaging is performed after fraction 20, if there is only a 0-20% reduction in the average volume of the elevated sub-volumes, and if there has been an absolute reduction of 1.1-1.5 in the average intensity values of each voxel, then there is only a 40+/−8% chance of 10-year disease-free survival.

INFERENCE ENGINE 120 EXAMPLE 4

If all of the criteria in EXAMPLE 3 are met, except that there has been a 21-40% reduction in the height of the largest sub-volume, and a 21-40% reduction in the volume of the largest sub-volume, then there is a 50+/−5% chance of complete metabolic atrophy of that sub-volume within 2 years. As stated above, the Diagnostics and Outcome Inference Engine 120 is also capable of providing diagnostic likelihood values.

INFERENCE ENGINE 120 EXAMPLE 5

If the indeterminate lesion in question is located in the prostate, if digital examination of the prostate does not reveal a suspicious nodule nor area of asymmetry, if the PSA is 5.1-10.0, if the race is African American, if the PSA doubling time is less than 1 year or unknown, if the imaging being performed is MRSI and intensity values represent normalized molecular concentration values, if isonumeric contours represent the sum of choline+citrate normalized concentration values, if an elevated sub-volume is present, if the largest elevated sub-volume is greater than or equal to 3 cc but less than 6 cc, if the established diagnostic challenge regimen is one 50 mg tablet of Casodex, if re-imaging is performed within one week of diagnostic challenge administration, and if the height of the largest elevated sub-volume decreases by greater than or equal to 20%, the likelihood of prostate cancer is 87%, +/−7%.

Rules in the knowledge base 139 that support the testing inference engine 124 will examine the case study storage 106 to determine if further information regarding the tumor is needed and then propose one or more tests. For example, a rule will determine if the cancer type has been determined. If not, other rules will examine data in the case study storage 106 and propose testing that is then indicated at process block 126. In addition, in the Testing Inference Engine 124, rules may examine the previously generated diagnostic likelihood values produced by the Diagnostics and Outcome Inference Engine 120.

INFERENCE ENGINE 124 EXAMPLE 1

If patient is female, if the organ containing the lesion in question is the breast, if patient is greater than or equal to 40 years old, if patient has 0-2 first degree relatives with a history of breast cancer, and if the Diagnostics and Outcome Inference Engine 120 suggests that the probability of cancer is less than 90%, proceed to biopsy. However, the Testing Inference Engine 124 will not always recommend a test. Instead, it can state whether a test is recommended.

INFERENCE ENGINE 124 EXAMPLE 2

If patient is female, if the organ containing the lesion in question is the breast, if patient is greater than or equal to 40 years old, if patient has 0-2 first degree relatives with a history of breast cancer, and if the Diagnostics and Outcome Inference Engine 120 suggests that the probability of cancer is 90% or greater, proceed directly to surgical excision and axillary lymph node sampling, without biopsy.

The rules knowledge base 141 that supports the therapy inference engine 127 draws on knowledge of the outcomes of various treatment protocols for particular cancer types, tumor location, tumor stage, tumor volume, number of sub-volumes, etc. Such rules examine the case study storage 106 for the needed information and when conditions are met, one or more therapies are proposed as indicated at process block 128.

Inference engine 127 can make recommendations regarding chemotherapy, radiation therapy, other cancer therapies, or interventions that can modify the effects of cancer therapy, such as the addition of a radiosensitizer or the transfusion of blood. In addition to the examination of information stored in case study storage 106, rules in knowledge base 141 that supports the inference engine 127, can examine the probability outcome values 122 generated by the diagnostics and outcome inference engine 120.

INFERENCE ENGINE 127 EXAMPLE 1

For the scenario described above in Inference Engine 120 example 1, if the odds of complete response are less than or equal to 60%, add two additional cycles of cetuximab prior to radiation therapy.

INFERENCE ENGINE 127 EXAMPLE 2

For the scenario described above in Inference Engine 120 example 2, if the odds of two-year local control are less than 70%, eliminate cetuximab from remainder of regimen.

INFERENCE ENGINE 127 EXAMPLE 3

For the scenario described above in Inference Engine 120 example 3, if the odds of 10-year disease-free survival are less than 60%, increase total number of radiation fractions to 48, to deliver a total of 86.5 Gy, and add 2 years of total androgen blockade after radiation therapy is complete.

INFERENCE ENGINE 127 EXAMPLE 4

For the scenario described above in Inference Engine 120 example 4, if the chance of complete metabolic atrophy of the sub-volume within 2 years is less than 60%, and if the sub-volume is located at least 1.0 cm from rectal and bladder interfaces, dose-paint sub-volume base with 5 mm margin, including contents, to 2.1 Gy per fraction for final 25 fractions. Ensure bladder and rectal interfaces do not exceed a total of 86 Gy.

The significant contours inference engine 130 is supported by a rules knowledge base 143 that brings to the clinician's attention any tumor contours or sub-volume contours of particular interest. When such a rule is satisfied, the subject tumor contour or sub-volume contour is displayed as indicated at process block 132. For example, a rule applicable to prostate cancer determines from data in the case study storage 106 a predicted poor outcome based on change in peak value and change in volume of the larges elevated sub-volume in a tumor. Display of the contour defining this sub-volume along with the contour defining the tumor boundary or ROI is produced on the display 12 or exported for remote viewing by multiple viewers.

The Significant Contour Inference Engine is also relevant to diagnosis. In addition to giving diagnostic likelihood values for an entire tumor or ROI, the Diagnostics and Outcomes Inference Engine 120 described above can give diagnostic likelihood values for specific sub-volumes that are stored in the case study storage 106. Contours particularly likely or unlikely to contain cancer are automatically displayed by the Significant Contours Inference Engine 130 based on this information.

INFERENCE ENGINE 130 EXAMPLE 1

For the scenario described above pertaining to Inference Engine 120 example 5, a contour forming the base of the largest elevated sub-volume, which likely contains cancer, can be selected. Based on the degree of change, however, contours can be placed (in accordance with rules) at the adjacent inside or outside contour, or around other areas within the prostate that are likely to contain cancer. Diagnostic likelihood values can be given for each selected contour. Following processes outlined earlier, a contour particularly likely to contain cancer is automatically selected and displayed along with the Testing Inference Engine results such as "Biopsy displayed contour."

If radiation therapy has been suggested, rules in the knowledge base 145 support a contours targeting inference engine 134 that produces an appropriate target contour as indicated at process block 136. For example, a rule may determine that "if" one level of radiation is to be applied to the entire tumor and a higher level of radiation is to be applied to a sub-volume, "then" produce a target contour of the tumor boundary and a target contour of the sub-volume boundary. In the preferred embodiment the radiation target indicated by the knowledge base 145 and case study storage 106 is displayed as a color contour superimposed on an anatomic image of the tumor and surrounding region. As indicated above, the system can interface with a targeting system through the therapeutic driver 42 and the target contour can also be exported to a radiation therapy or surgical guidance system.

INFERENCE ENGINE 134 EXAMPLE 1

For the scenario described above pertaining to Inference Engine 120 example 4 and Inference Engine 127 example 4 in which MRSI is used for targeting radiation therapy in the setting of prostate cancer, and the recommendation is made to dose-paint a sub-volume base (with 5 mm margin), including contents, to 2.1 Gy for the final 25 fractions if the chance of complete metabolic atrophy within 2 years is less than 60%, this contour is automatically displayed for targeting. In this example, the inference engine 134 displays the key contour for targeting or the contour providing 5 mm of margin around the key contour, or both.

Figure 9A:
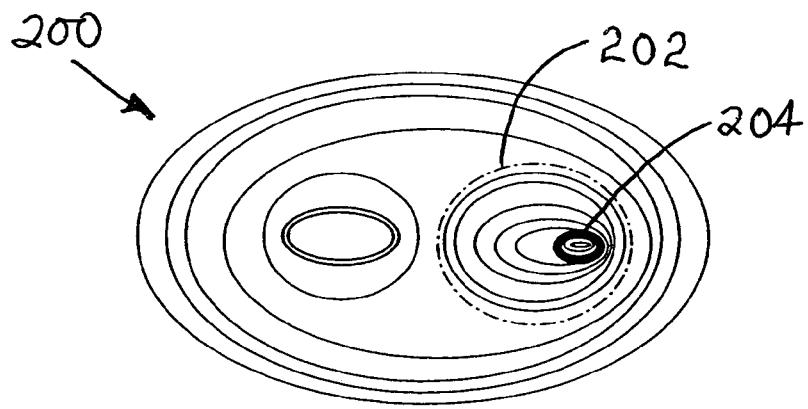
FIGS. 9A-9C are isonumeric images of a tumor at different stages of its treatment.

This function may be better explained visually. Referring to FIG. 9A a three-dimensional isonumeric image is produced from the acquired image. A two-dimensional significant tumor contour 200 is displayed by the expert system 112. A sub-volume indicated by dashed contour line 202 has been parameterized and the expert system 112 has indicated it should received extra radiation dose per treatment via intensity modulated dose-painting, due to the distance between it and adjacent outside tumor boundary contour, volume and surface area differences between it and adjacent outside contour, and number of higher-threshold contours contained within it. The expert system 112 tentatively selects bold contour 204 for stereotactic boosting at the end of radiation therapy, due to the very small distance between it and very-high threshold contours contained within it.

Figure 9B:
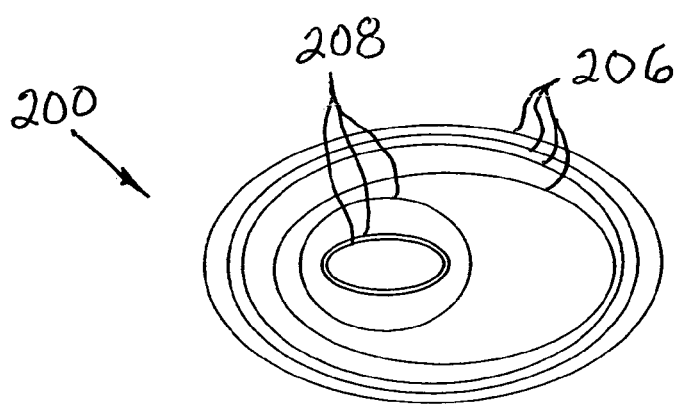

Referring to FIG. 9B, the patient is re-imaged midway through radiation treatment and the sub-volume 202 is no longer present within the significant tumor contour 200. The outer contours 206 have become smaller in size, but the inner contours 208 have remained substantially the same and are demonstrating early radioresistance. Due to this radioresistance indicated by the isonumeric image parameters, the expert system 112 selects the sub-volume within these inner contour lines 208 for intensity-modulated dose-painting.

Figure 9C:
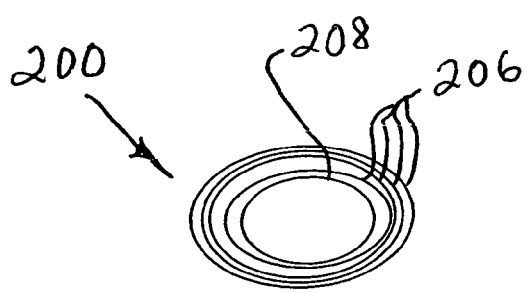

Referring particularly to FIG. 9C, the patient is re-imaged at the end of external beam radiation and the significant tumor contour 200 reveals that the outer contours 206 have shrunk in size and only the lowest threshold level contour 208 of the three inner contours 208 remains. The expert system 112 indicates that this entire tumor contour 200 should be targeted for stereotactic boost. In this embodiment, radiation therapy is used as the targeting technology. However, one can see that this invention is equally relevant to other targeting technologies, to include radiofrequency ablation, stereotactically-guided surgical ablation, and many others.

While the preferred embodiment of this invention relies primarily on change, and on calculation of change values, other embodiments integrate measured tumor parameters (usually from a pre-treatment image), without change. Tumor parameters can be calculated. If desired, parameters can be directly integrated into a tumor or other ROI expression model that is not change-based. Parameters can be fed directly to Case Study Storage 106 as seen in FIG. 2. These additional parameters are also used by the Diagnostics and Outcome, Testing, Therapy, Significant Contours, and Contours Targeting inference Engines. Using such parameters a first prognosis can be predicted, before any therapy is initiated. A particularly poor prognosis could prompt the recommendation for more aggressive chemotherapy, starting with cycle 1. Or, a particular sub-volume may be identified, before therapy is initiated, that is unlikely to respond fully to radiation therapy. The recommendation could be made to dose-paint the sub-volume to a higher dose per fraction, beginning with fraction one of radiation therapy. Or, the isonumeric contour profile of a patient with newly diagnosed non-Hodgkins lymphoma could be used to predict which histologic variant, and which grade, of lymphoma is present.

While integrating numerically-represented changes in imaging data represented by the isonumeric contour format is the preferred approach for this invention, the invention is also applicable to imaging data in other formats for which features and change can be numerically-expressed, and to numerically-expressed changes in non-image-based data (such as changes in serum tumor marker values).

While the expert system 112 as described herein generally makes recommendations specifically related to cancer therapy, it can also make recommendations related to supportive care, such as "transfuse 2 units of packed red blood cells before initiating therapy" or "wait until hemoglobin level is at least 11.0 before continuing therapy." In addition, it can recommend an intervention, such as transfusion or the addition of a radiosensitizing drug, that will modify the effect of therapy.

It should be apparent that many of these processes can be combined. For example, drug therapy guidance, radiation therapy guidance, or guidance of radiation therapy given concurrently with drug therapy (such as chemotherapy) can be both image- and non-image-based, and both change-based and static (based on data generated at a single point in time). In addition, change values specifically related to the tumor can be combined with change values related to other data, such as neutrophil count or pharmacokinetic drug measurements, can be combined within the case study storage 106 and examined by rules in the expert system 112.

As described herein, this invention is used for cancer therapy. However, it is equally relevant to other pathologies that can be diagnosed via imaging, and/or for which imaging can be used to monitor therapy. For example, emerging data are proving the utility of imaging technologies such as brain MRSI and brain PET in diagnosing conditions such as bipolar disorder, Alzheimer's Disease, and movement disorders such as Parkinson's Disease. By creating isonumeric contours of brain or specific areas within the brain, by generating static or change-based isonumeric contour parameter data, and by applying the system described herein with a case study storage 106 and rules relevant to these conditions, these conditions can be diagnosed and managed. For example, by administering an agent that is expected to affect pathologic brain foci different than it affects normal brain, diagnostic percent likelihood values can be generated. Following the administration of therapy, outcomes can be predicted. Via analysis of change, abnormal areas within the brain can be defined. Therapy can be monitored, and new therapeutic interventions can be suggested. Resistant foci can be identified and outlined, and suggestions related to targeting the resistant foci can be made (such as deep brain stimulation, radiosurgical ablation, or stereotactic surgical ablation or administration of local drug).

We claim:

1. A tumor analysis system which comprises:
    means for importing an image of a tumor;
    means for producing from the imported image an isonumeric image that depicts a contour indicative of locations in the imported image having a selected threshold value of a tumor parameter;
    a case study storage for storing isonumeric images;
    means for calculating changes in the tumor depicted in the imported image by comparing the isonumeric image produced from the imported image with previously produced isonumeric images stored in the case study storage and storing the changes in the case study storage; and
    an expert system for analyzing the tumor using information stored in the case study storage.

2. The system as recited in claim 1 in which the expert system includes a rules knowledge base and an inference engine, and in which the inference engine is operable in response to information received from the rules knowledge base to examine information in the case study storage and produce information regarding one of diagnosis, testing and treatment of the tumor.

3. The system as recited in claim 1 which includes means for calculating tumor parameters from the isonumeric image and storing them in the case study storage.

4. The system as recited in claim 3 in which a sub-volume is identified in the isonumeric image and parameters related to the sub-volume are calculated and stored in the case study storage.

5. The system as recited in claim 4 in which the expert system separately analyzes the sub-volume and produces information regarding one of diagnosis, testing and treatment that is distinct from information regarding one of diagnosis, testing, and treatment of the tumor as a whole.

6. A tumor analysis system which comprises:
    means for importing an image of a tumor;
    means for calculating from this image values of parameters that measure the tumor;
    a case study storage for storing the calculated parameters;
    means for calculating changes that have occurred in tumor parameters based on parameters previously stored in the case study storage; and
    an expert system for producing a target contour for further treatment of the tumor based on information in the case study storage.

7. The system as recited in claim 6 in which the expert system includes a rules knowledge base and an inference engine that receives information from the case study storage and information from the rules knowledge base.

8. The system as recited in claim 6 in which one of the calculated parameters is a sub-volume of the tumor and the target contour is limited to the sub-volume.

9. A method for analyzing a pathology, the steps comprising:
    a) importing an image of the pathology;
    b) producing an isonumeric image of the imported image that depicts a contour indicative of locations in the imported image having a selected threshold value of a pathology parameter;
    c) storing the isonumeric image in a case study storage;
    d) calculating parameters related to the pathology from the stored isonumeric image; and
    e) analyzing the pathology with an expert system that examines parameters stored in the case study storage using rules stored in a rules knowledge base.

10. The method as recited in claim 9 in which step d) includes calculating changes in the pathology by comparing the stored isonumeric image with previously produced isonumeric images stored in the case study storage.

11. The method as recited in claim 9 in which step d) includes calculating parameters related to a sub-volume of the pathology depicted in the stored isonumeric image.

12. The method as recited in claim 11 in which step e) includes examining parameters related to the sub-volume and producing an indication based on the examination.

* * * * *

UNITED STATES PATENT AND TRADEMARK OFFICE
CERTIFICATE OF CORRECTION

PATENT NO. : 7,606,405 B2  Page 1 of 1
APPLICATION NO. : 11/417080
DATED : October 20, 2009
INVENTOR(S) : Sawyer et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 533 days.

Signed and Sealed this

Twelfth Day of October, 2010

David J. Kappos
*Director of the United States Patent and Trademark Office*